US012691251B2

(12) United States Patent (10) Patent No.: US 12,691,251 B2
Okawa (45) Date of Patent: Jul. 28, 2026

(54) GUIDING CATHETER

(71) Applicant: JAPAN LIFELINE CO., LTD., Tokyo (JP)

(72) Inventor: Yasuhiro Okawa, Tokyo (JP)

(73) Assignee: JAPAN LIFELINE CO., LTD., Tokyo (JP)

(*) Notice: Subject to any disclaimer, the term of this patent is extended or adjusted under 35 U.S.C. 154(b) by 629 days.

(21) Appl. No.: 18/026,923

(22) PCT Filed: Oct. 23, 2020

(86) PCT No.: PCT/JP2020/039980
§ 371 (c)(1),
(2) Date: Mar. 17, 2023

(87) PCT Pub. No.: WO2022/085199
PCT Pub. Date: Apr. 28, 2022

(65) Prior Publication Data
US 2023/0321396 A1 Oct. 12, 2023

(51) Int. Cl.
*A61M 25/00* (2006.01)
*A61M 25/06* (2006.01)
*A61M 25/10* (2013.01)

(52) U.S. Cl.
CPC ...... *A61M 25/005* (2013.01); *A61M 25/0032* (2013.01); *A61M 25/0097* (2013.01);
(Continued)

(58) Field of Classification Search
CPC ............ A61M 25/005; A61M 25/0032; A61M 25/0097; A61M 2025/0037;
(Continued)

(56) References Cited

U.S. PATENT DOCUMENTS 10,286,308 B2 5/2019 Sawyer et al.
11,507,251 B2 11/2022 Uy et al.
(Continued)

FOREIGN PATENT DOCUMENTS

JP H02209159 A 8/1990
JP H07265433 A 10/1995
(Continued)

OTHER PUBLICATIONS

An Office Action in corresponding JP Application No. 2022-556365 dated Jul. 11, 2023 is attached, 4 pages.
(Continued)

*Primary Examiner* — Chelsea E Stinson
*Assistant Examiner* — Hamza A Darb
(74) *Attorney, Agent, or Firm* — Shih IP Law Group, PLLC

(57) ABSTRACT

A guiding catheter includes: a shaft that includes a main lumen and a sub-lumen; a balloon attached to a distal end portion of the shaft; a distal end tip connected to a distal end side of the shaft; and a hub connected to a proximal end side of the shaft. The shaft is formed by layering: an inner layer that forms the main lumen; a first reinforcing layer formed on the inner layer; an intermediate layer formed on the first reinforcing layer and enclosing the sub-lumen; a second reinforcing layer formed on the intermediate layer; and an outer layer formed on the second reinforcing layer from a proximal end to a distal end.

6 Claims, 7 Drawing Sheets

(52) U.S. Cl.
CPC ............... *A61M 2025/0037* (2013.01); *A61M 2025/1061* (2013.01); *A61M 2025/1079* (2013.01)

(58) Field of Classification Search
CPC .. A61M 2025/1061; A61M 2025/1079; A61M 25/0045; A61M 25/104; A61M 25/0662
See application file for complete search history.

(56) References Cited

U.S. PATENT DOCUMENTS

| | | | |
|---|---|---|---|
| 2007/0010787 A1* | 1/2007 | Hackett | A61M 25/005 604/96.01 |
| 2007/0265433 A1 | 11/2007 | Moore et al. | |
| 2012/0196498 A1 | 8/2012 | Ochiai | |
| 2013/0066720 A1 | 3/2013 | Schwarz | |
| 2015/0306805 A1* | 10/2015 | Dando | B29C 48/902 264/171.23 |
| 2016/0116814 A1 | 4/2016 | Teranishi et al. | |
| 2017/0093903 A1 | 3/2017 | Sakalanaga et al. | |
| 2019/0184135 A1* | 6/2019 | Shimizu | A61M 25/0069 |
| 2022/0031342 A1* | 2/2022 | Conway | A61M 25/1034 |

FOREIGN PATENT DOCUMENTS

| | | |
|---|---|---|
| JP | H1071208 A | 3/1998 |
| JP | H10286308 A | 10/1998 |
| JP | H11507251 A | 6/1999 |
| JP | 2001508670 A | 7/2001 |
| JP | 2012196498 A | 10/2012 |
| JP | 2013066720 A | 4/2013 |
| JP | 2016116814 A | 6/2016 |
| JP | 2016527013 A | 9/2016 |
| JP | 2017093903 A | 6/2017 |

OTHER PUBLICATIONS

Office Action issued for corresponding Japanese Patent Application No. 2022-556365 with Machine Translation dated Jan. 16, 2024.

Japanese Office Action dated Sep. 19, 2023 in Application No. 2022-556365, 4 pages.

International Search Report for the corresponding PCT Application No. PCT/JP2020/039980 with English translation, dated Nov. 13, 2020, 6 pages.

International Preliminary Examination Report on Patentability (I) with an English translation, dated Apr. 13, 2023 11 pages.

* cited by examiner

GUIDING CATHETER

CROSS-REFERENCE TO RELATED APPLICATIONS

This application is based upon and claims the benefit of priority from the International Patent Application No. PCT/JP2020/039980, filed on Oct. 23, 2020, the entire content of each of which is incorporated herein by reference.

BACKGROUND

Field of the Invention

The present invention relates to a guiding catheter in which a balloon is attached to a distal end portion.

Description of the Related Art

Conventionally, a guiding catheter has been used to insert a tubular medical instrument used for intravascular treatment and deliver the medical instrument to a predetermined position inside a body.

There has been also known a guiding catheter in which a balloon for temporarily blocking a blood flow during intravascular treatment is attached to a shaft distal end portion (see Patent Literatures 1 and 2 below).

A guiding catheter with balloon includes a shaft, a balloon attached to a distal end portion of the shaft, a distal end tip connected to the distal end side of the shaft, and a hub connected to a proximal end side of the shaft. The shaft constituting the guiding catheter is formed with a main lumen for inserting a tubular medical instrument and a sub-lumen for flowing a fluid for expanding the balloon.

Patent Literature 1: JP 2013-66720 A

Patent Literature 2: JP 2001-508670 T

A guiding catheter is inserted into a curved blood vessel while searching for a target blood vessel (a blood vessel for delivering the medical instrument) to reach its distal end to an entrance of the target blood vessel.

Good torque transmission performance is demanded for the guiding catheter that performs such an operation.

Here, as means for imparting torque transmission performance to the catheter, the shaft has been reinforced by a coil or a braid. The guiding catheters described in Patent Literatures 1 and 2 also employ such reinforcing means.

However, the conventional guiding catheters including those described in Patent Literatures 1 and 2 do not have sufficient torque transmission performance.

In particular, in the guiding catheter of Patent Literature 1, since a proximal end portion and a distal end portion of the shaft are reinforced with respective different coils, the torque transmission performance from the proximal end to the distal end is extremely poor. Although the guiding catheter of Patent Literature 2 is reinforced with a continuous braid from a proximal end to a distal end of a shaft, its torque transmission performance is not sufficient.

In the guiding catheter inserted into a blood vessel, the shaft may follow the blood vessel shape to bend. At this time, a sub-lumen may crush, possibly failing to flow a fluid for expanding the balloon.

In particular, in the guiding catheter of Patent Literature 2, the sub-lumen is disposed outside the braid, so there is an extremely high possibility that the sub-lumen crushes.

SUMMARY OF THE INVENTION

The present invention has been made on the basis of the above-described circumstances.

An object of the present invention to provide a guiding catheter that has superior torque transmission performance than the conventionally known guiding catheter with balloon and that does not crush a sub-lumen for expanding a balloon even when a shaft bends.

A guiding catheter to the present invention is a guiding catheter with balloon that includes a shaft, a balloon, a distal end tip, and a hub. The shaft includes a main lumen and a sub-lumen. The balloon is attached to a distal end portion of the shaft and expands by supplying a fluid flowing through the sub-lumen to an inside of the balloon. The distal end tip that is connected to a distal end side of the shaft and includes a lumen communicating with the main lumen and opening at a distal end of the distal end tip. The hub is connected to a proximal end side of the shaft and includes ports communicating with the respective main lumen and sub-lumen. The shaft is formed by layering an inner layer that forms the main lumen, a first reinforcing layer formed on the inner layer, an intermediate layer that is formed on the first reinforcing layer and encloses the sub-lumen, a second reinforcing layer formed on the intermediate layer, and an outer layer formed on the second reinforcing layer from a proximal end to a distal end.

BRIEF DESCRIPTION OF DRAWINGS

Embodiments will now be described, by way of example only, with reference to the accompanying drawings which are meant to be exemplary, not limiting, and wherein like elements are numbered alike in several Figures, in which.

Figure 1:
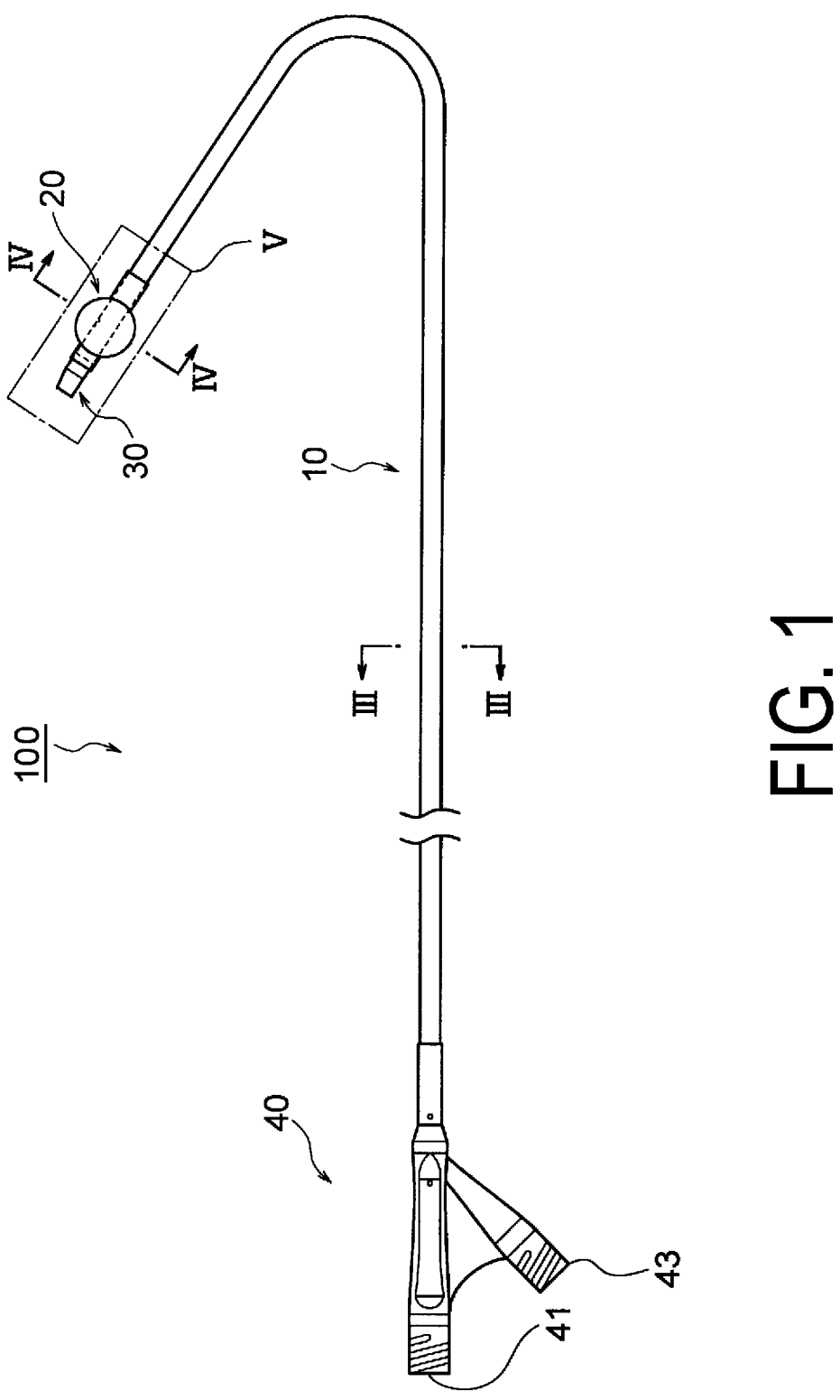
FIG. 1 is a front view illustrating an embodiment of a guiding catheter according to the present invention.

DETAILED DESCRIPTION OF THE INVENTION (1) A guiding catheter to the present invention is a guiding catheter with balloon that includes a shaft, a balloon, a distal end tip, and a hub. The shaft includes a main lumen and a sub-lumen. The balloon is attached to a distal end portion of the shaft and expands by supplying a fluid flowing through the sub-lumen to an inside of the balloon. The distal end tip that is connected to a distal end side of the shaft and includes a lumen communicating with the main lumen and opening at a distal end of the distal end tip. The hub is connected to a proximal end side of the shaft and includes ports communicating with the respective main lumen and sub-lumen. The shaft is formed by layering an inner layer that forms the main lumen, a first reinforcing layer formed on the inner layer, an intermediate layer that is formed on the first reinforcing layer and encloses the sub-lumen, a second reinforcing layer formed on the intermediate layer, and an outer layer formed on the second reinforcing layer from a proximal end to a distal end.

According to the guiding catheter having the configuration, the shaft constituting it is reinforced by the two reinforcing layers (the first reinforcing layer and the second reinforcing layer) formed from the proximal end to the distal end, and thus superior torque transmission performance can be expressed compared to the conventional guiding catheter.

Additionally, since the sub-lumen formed in the shaft is enclosed in the intermediate layer between the first reinforcing layer and the second reinforcing layer, the sub-lumen protected by being interposed between two reinforcing layers does not crush even when the shaft is bent.

(2) In the guiding catheter to the present invention, the following is preferred from an aspect of expressing superior torque transmission performance. Both of the first reinforcing layer and the second reinforcing layer are braided layers formed of braided tubes that are continuous from the proximal end to the distal end of the shaft.

(3) In the guiding catheter to the present invention, the following is preferred. The main lumen is eccentric with respect to a central axis of the shaft. The sub-lumen is formed on a side opposite to a side where the main lumen is eccentric. A cross-section of the sub-lumen is substantially a rectangle or a crescent.

With the guiding catheter having the configuration, a diameter of the shaft can be sufficiently reduced.

(4) In the guiding catheter to the present invention, the following is preferred. The shaft has a distal end portion where shaping is performed in a bent or curved shape.

(5) In the guiding catheter of (4) above, the following is preferred from aspects of ease of shaping (facilitates bending) and preventing the sub-lumen from crushing. Shaping is performed such that the sub-lumen is located outside the bent or curved shape.

(6) In the guiding catheter to the present invention, the following is preferred. The distal end tip includes a proximal end portion having an outer diameter same as an outer diameter of the shaft and a distal end portion decreasing in diameter in a distal end direction. A protrusion portion that is inserted into the sub-lumen of the shaft and occludes a distal end opening of the sub-lumen is formed at a proximal end of the distal end tip.

The guiding catheter having the configuration allows reliably occluding the distal end of the sub-lumen and, for example, a drop of the distal end tip can be preferably prevented.

(7) In the guiding catheter of (6) above, the following is preferred. A ring-shaped contrast marker is inserted into and fitted to the lumen of the distal end tip at the proximal end portion.

(8) In the guiding catheter to the present invention, both of the first reinforcing layer and the second reinforcing layer may be coil layers continuous from the proximal end to the distal end of the shaft.

(9) In the guiding catheter of (8) above, the following is preferred from an aspect of expressing superior torque transmission performance not affected by a rotation direction. A winding direction of a coil constituting the first reinforcing layer and a winding direction of a coil constituting the second reinforcing layer are mutually opposite.

EMBODIMENTS

An embodiment of the present invention will be described below with reference to the drawings.

A guiding catheter of the present embodiment is a guiding catheter to insert a tubular medical instrument used for intravascular treatment and deliver the medical instrument to a predetermined position inside a body.

A guiding catheter 100 according to the present embodiment illustrated in FIGS. 1 to 6 includes: a shaft 10 that includes a main lumen 101 and a sub-lumen 102; a balloon 20 that is attached to a distal end portion of the shaft 10 and expands by supplying a fluid flowing through the sub-lumen 102 to an inside of the balloon 20; a distal end tip 30 that is connected to a distal end side of the shaft 10 and includes a lumen 301 communicating with the main lumen 101 and opening at a distal end of the distal end tip; and a hub 40 that is connected to a proximal end side of the shaft 10 and includes a main port 41 communicating with the main lumen 101 and an expansion port 43 communicating with the sub-lumen 102. The shaft 10 is formed by layering an inner layer 11 that partitions and forms the main lumen 101, a first braided layer 12 formed on the inner layer 11, an intermediate layer 13 formed on the first braided layer 12 so as to enclose the sub-lumen 102, a second braided layer 14 formed on the intermediate layer 13, and an outer layer 15 formed on the second braided layer 14 from the proximal end to the distal end.

The guiding catheter 100 includes the shaft 10, the balloon 20, the distal end tip 30, and the hub 40.

Figure 2:
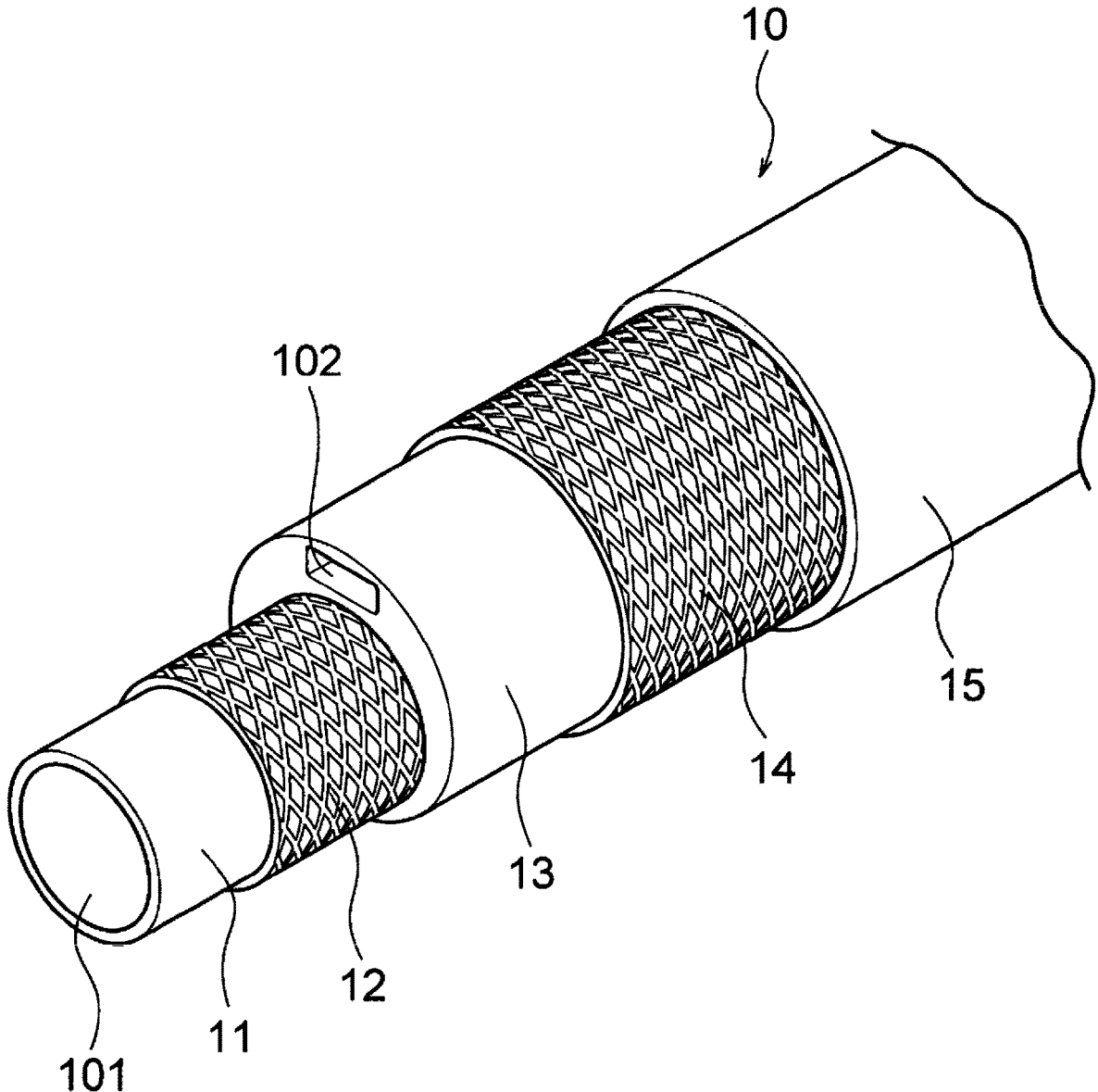
FIG. 2 is a perspective view illustrating a layer configuration of a shaft of the guiding catheter illustrated in FIG. 1.
Figure 3:
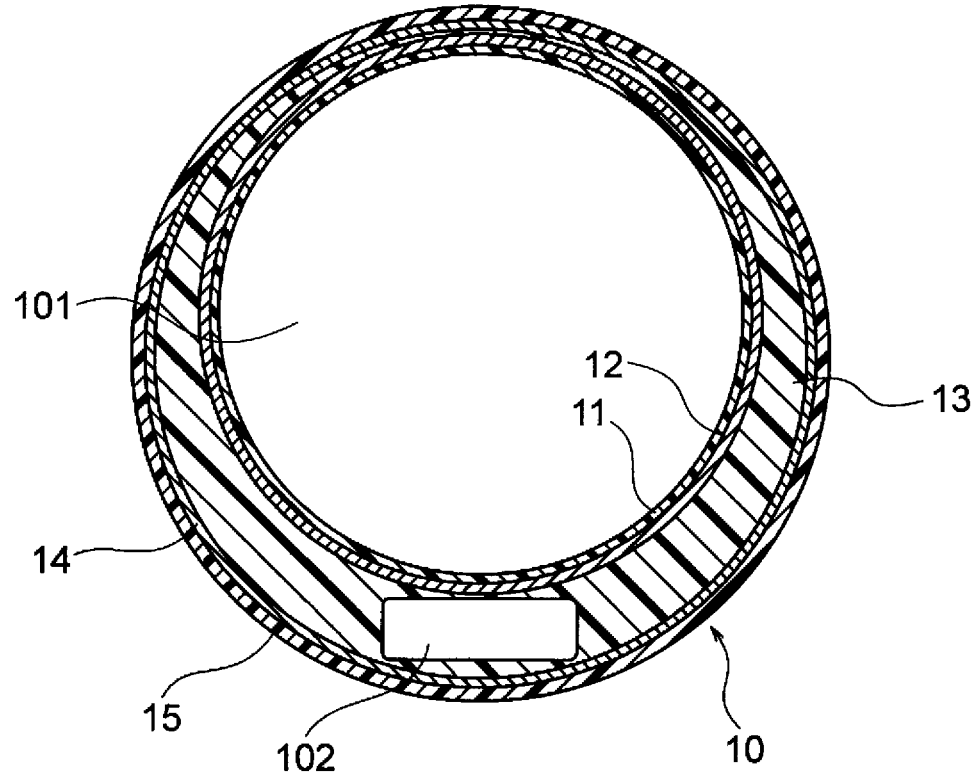
FIG. 3 is a cross-sectional view taken along in FIG. 1.
Figure 4:
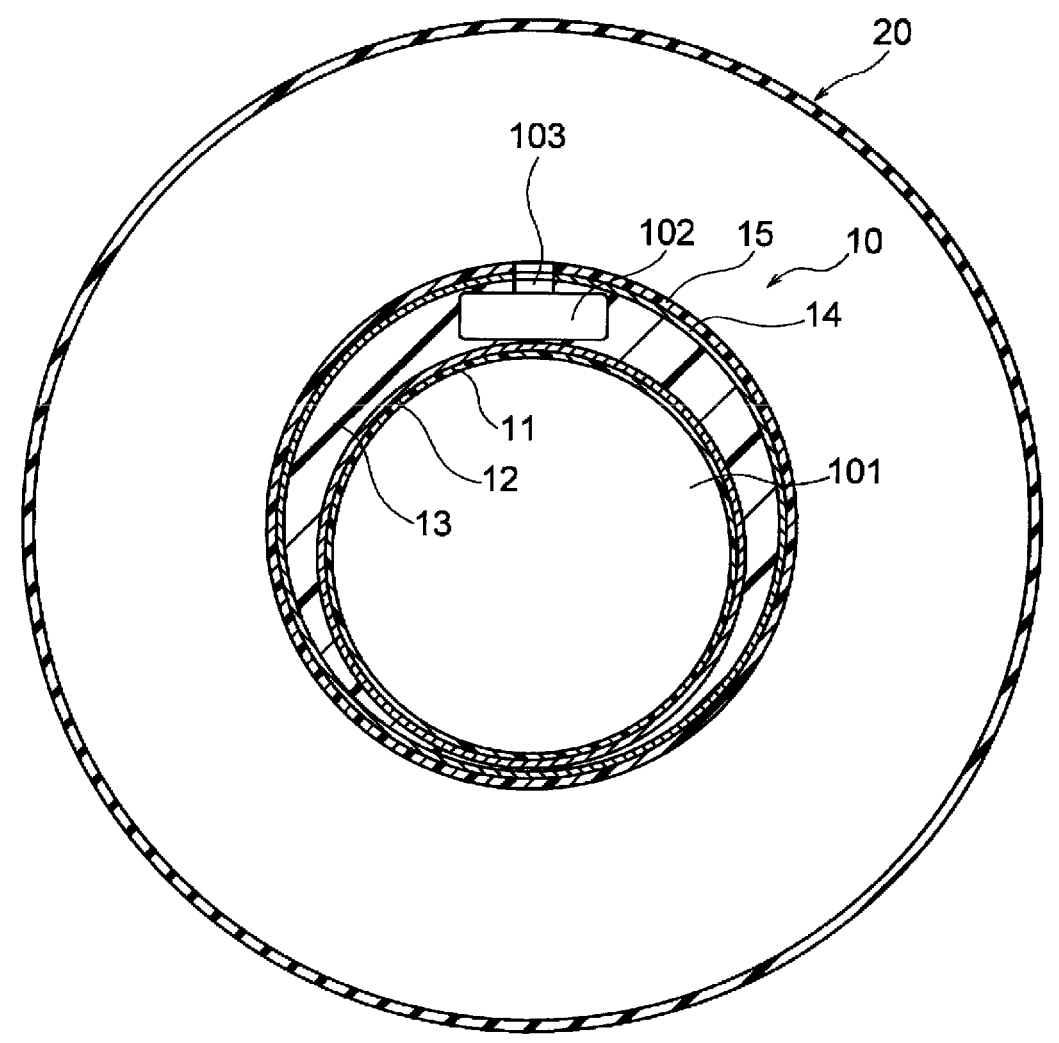
FIG. 4 is a cross-sectional view taken along IV-IV in FIG. 1.

As illustrated in FIGS. 2 to 4, the main lumen 101 and the sub-lumen 102 are formed in the shaft 10 constituting the guiding catheter 100.

The main lumen 101 is a lumen for inserting a tubular medical instrument, such as a microcatheter, and is formed eccentric with respect to a central axis of the shaft 10.

The sub-lumen 102 is formed on the side opposite to the side where the main lumen 101 is eccentric. The cross-section of the sub-lumen 102 is a rectangle.

By disposing the main lumen 101 and the sub-lumen 102 in this manner, the cross-sectional area of the main lumen 101 (an insertion passage of the medical instrument) and the cross-sectional area of the sub-lumen 102 (a fluid flow path) can be sufficiently ensured, and the diameter of the shaft 10 can be sufficiently reduced.

The shaft 10 is formed by stacking the inner layer 11, the first braided layer 12, the intermediate layer 13, the second braided layer 14, and the outer layer 15, and this layer configuration is the same from the proximal end to the distal end of the shaft 10.

The inner layer 11 of the shaft 10 is a resin tube (lumen tube) that forms the main lumen 101.

The resin constituting the inner layer 11 can include a fluorine-based resin, such as polytetrafluoroethylene (PTFE) or perfluoroalkoxy alkane (PFA).

The inner diameter of the inner layer 11, which is the diameter of the main lumen 101, is usually from 1.0 to 3.0 mm, and preferably from 1.7 to 2.5 mm.

The thickness of the inner layer 11 is usually from 5 to 50 μm, and preferably from 15 to 40 μm.

The first braided layer 12 is formed on the outer periphery of the inner layer 11. The first braided layer 12 is formed of a braided tube formed continuously from the proximal end to the distal end of the shaft 10 by weaving a metal wire, such as stainless steel.

For example, the outer diameter (the wire diameter), the number of carriers, and the number of ends of the metal wire constituting the braided tube can be adjusted appropriately in accordance with required reinforcement performance.

Note that the cross-sectional shape of the metal wire is not limited to a circle and may be a rectangle.

The thickness of the first braided layer 12 is usually from 20 to 100 μm and preferably from 30 to 60 μm.

The intermediate layer 13 enclosing the sub-lumen 102 is formed on the outer periphery of the first braided layer 12.

The intermediate layer 13 is made of resin. The resin constituting the intermediate layer 13 can include a thermoplastic resin, such as polyamide, polyamide elastomer, polyether polyamide, polyether block amide (PEBAX [registered trademark]), nylon, and polyurethane.

Since the main lumen 101 (the inner layer 11 and the first braided layer 12) is eccentric with respect to the central axis of the shaft 10, the thickness of the intermediate layer 13 is different in the circumferential direction.

The sub-lumen 102 is enclosed in the side (the thick portion of the intermediate layer 13) opposite to the side where the main lumen 101 is eccentric.

A preferred example of the dimension of the cross-sectional shape (rectangle) of the sub-lumen 102 is 0.30 mm×0.90 mm.

The second braided layer 14 is formed on the outer periphery of the intermediate layer 13. The second braided layer 14 is formed of a braided tube similar to the first braided layer 12.

The thickness of the second braided layer 14 is usually from 20 to 100 μm, and preferably from 30 to 60 μm.

The outer layer 15 is formed on the outer periphery of the second braided layer 14.

The outer layer 15 is made of resin. The resin constituting the outer layer 15 can include a resin similar to the constituent resin of the intermediate layer 13.

The thickness of the outer layer 15 is usually from 10 to 100 μm, and preferably from 30 to 70 μm.

The outer diameter of the outer layer 15, which is the outer diameter of the shaft 10, is usually from 2.0 to 4.0 mm, and preferably from 2.5 to 3.5 mm.

The hardness of the outer layer 15 is preferably from 40 to 80 as hardness with a D hardness tester. Note that the outer layer 15 may be made of resin having the same hardness along an axial direction, but may be integrally formed using resins having different hardnesses along the axial direction.

As illustrated in FIG. 1, the distal end portion of the shaft 10 is shaped in a bent shape.

In the distal end portion of the shaped shaft 10, the sub-lumen 102 (the thick portion of the intermediate layer 13) is located outside the bent shape (the outer peripheral side).

The sub-lumen 102 located outside the bent shape allows reliably preventing the crush of the sub-lumen 102. Additionally, the thin portion of the intermediate layer 13 located inside (the inner peripheral side) the bent shape allows ease of shaping.

Figure 5:
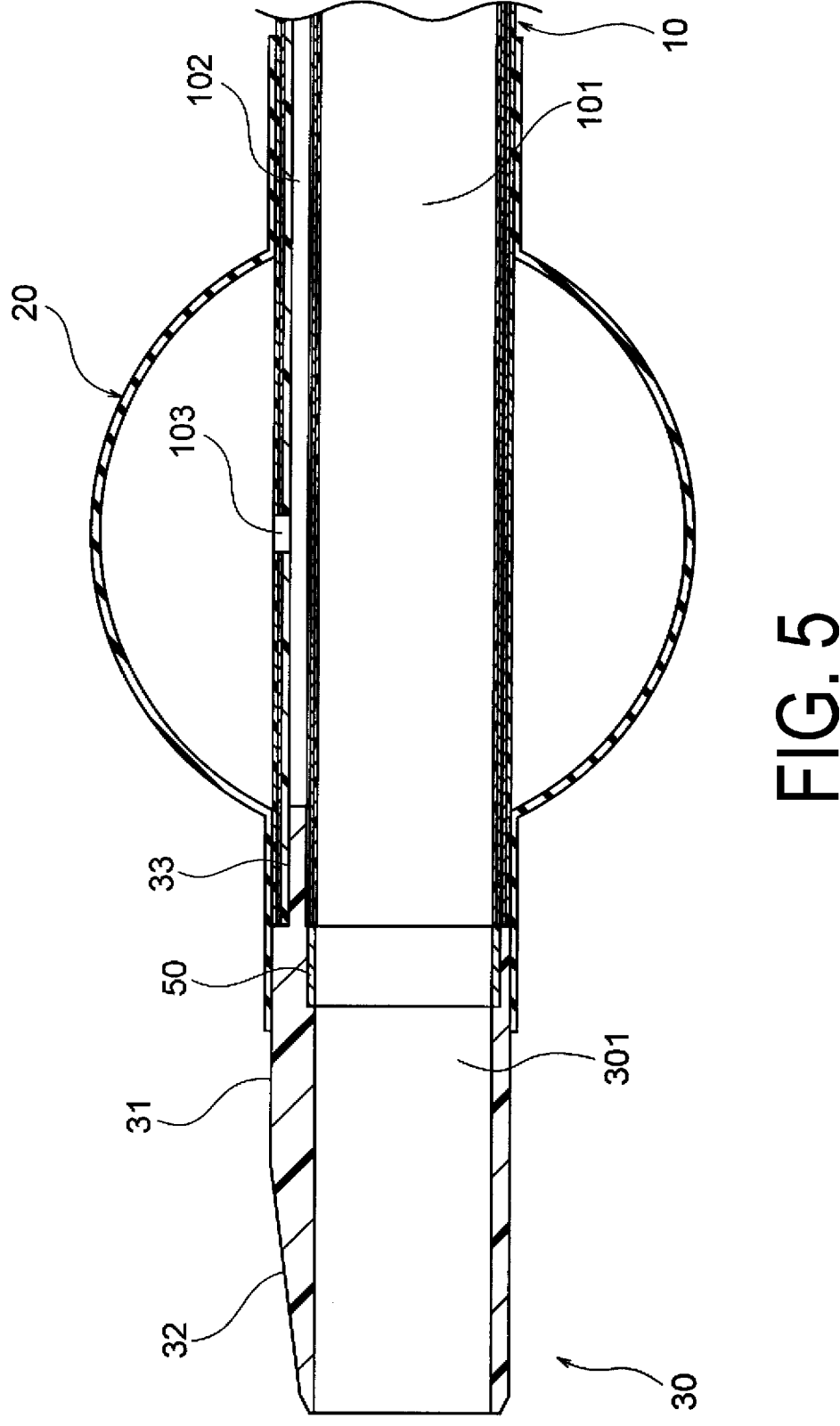
FIG. 5 is a vertical cross-sectional view illustrating a distal end portion of the guiding catheter illustrated in FIG. 1.
Figure 6:
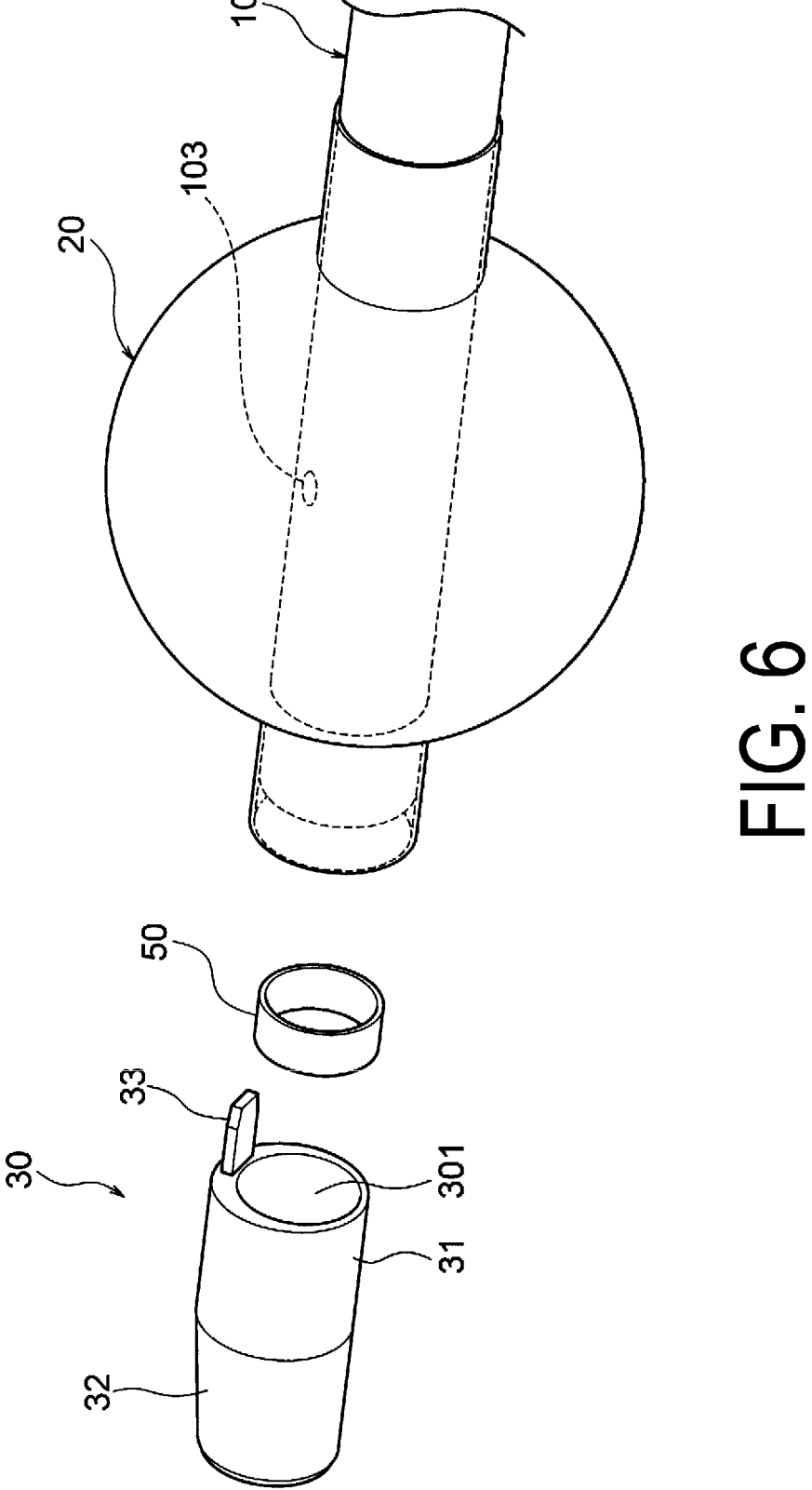
FIG. 6 is a perspective view illustrating components of the distal end portion of the guiding catheter illustrated in FIG. 1.

As illustrated in FIGS. 4 to 6, a side hole 103 communicating with the sub-lumen 102 is formed in the outer peripheral surface of the shaft 10 at the distal end portion on which the balloon 20 is mounted.

This allows the inflation fluid flowing through the sub-lumen 102 to flow outside the shaft 10 (the inside of the balloon 20) through the side hole 103.

The balloon 20 is attached to the distal end portion of the shaft 10.

The balloon 20 expands by the fluid flowing the sub-lumen 102 of the shaft 10 and flowing out from the side hole 103. Here, the fluid can include saline and a contrast agent.

The constituent material of the balloon 20 can include a thermoplastic resin, such as polyamide, polyether polyamide, PEBAX, nylon, and polyurethane.

The diameter (the maximum expansion diameter) of the balloon 20 during expansion is usually from 5 to 20 mm, and preferably from 8 to 15 mm.

The distal end tip 30 is connected to the distal end side of the shaft 10.

As illustrated in FIGS. 5 and 6, the distal end tip 30 includes a proximal end portion 31 having an outer diameter same as that of the shaft 10, and a distal end portion 32 that decreases in diameter in the distal end direction.

In the distal end tip 30, a lumen 301 that communicates with the main lumen 101 of the shaft 10 and opens at the distal end is formed.

A ring-shaped contrast marker 50 is inserted into and fitted to the lumen 301 of the distal end tip 30 at the proximal end portion 31.

The constituent material of the contrast marker 50 can include platinum and a platinum-based alloy. The inner diameter of the contrast marker 50 is the same as the diameter of the main lumen 101 of the shaft 10.

The diameter of the lumen 301 (except for a region where the contrast marker 50 is inserted and fitted) of the distal end tip 30 is same as the diameter of the main lumen 101 of the shaft 10.

The diameter of the lumen 301 in the region where the contrast marker 50 is inserted and fitted is slightly larger than the diameter of the main lumen 101 of the shaft 10. After the contrast marker 50 is inserted into and fitted to the lumen 301, a formation surface of the main lumen 101 of the shaft 10 and the inner peripheral surface of the contrast marker 50 are flush with a formation surface of the lumen 301.

As a result, since a step difference does not occur between the main lumen 101 of the shaft 10 and the lumen 301 of the distal end tip 30, the tubular medical instrument can be smoothly inserted.

In FIGS. 5 and 6, 33 denotes a protrusion portion extending from a proximal end surface of the distal end tip 30 (the proximal end portion 31) in the proximal end direction.

The distal end tip 30 and the shaft 10 are joined by thermal fusion, for example.

The protrusion portion 33 of the distal end tip 30 is inserted into the sub-lumen 102 of the shaft 10, and the distal end opening of the sub-lumen 102, which is a flow path of the fluid, is completely occluded by the protrusion portion 33. This makes it possible to reliably prevent a leakage of the fluid from the distal end of the sub-lumen 102.

Also, the protrusion portion 33 acting as a retainer allows preferably preventing the distal end tip 30 from dropping off from the shaft 10.

The constituent material of the distal end tip 30 can include the resin same as the resin constituting the intermediate layer 13 and the outer layer 15 of the shaft 10.

The hardness of the distal end tip 30 is lower than the hardness of the shaft 10 (the outer layer 15), and thus the guiding catheter 100 with flexible distal end portion has superior followability to the blood vessel shape.

The hub 40 is connected to the proximal end side of the shaft 10.

As illustrated in FIG. 1, the hub 40 includes the main port 41 that communicates with the main lumen 101 and the expansion port 43 that communicates with the sub-lumen 102.

According to the guiding catheter 100 of the present embodiment, the shaft 10 constituting it is reinforced by the two reinforcing layers of the first braided layer 12 and the second braided layer 14, and thus superior torque transmission performance can be expressed compared to the conventionally known guiding catheter with balloon.

Additionally, since the sub-lumen 102 enclosed in the intermediate layer 13 is protected by the first braided layer 12 and the second braided layer 14 so as to be interposed. Accordingly, even when the shaft 10 bends during insertion into a blood vessel, the sub-lumen 102 does not crush.

An embodiment of the present invention has been described above. However, a guidewire shaft of the present invention is not limited thereto, and various changes can be made.

For example, the cross-sectional shape of the sub-lumen needs not be a rectangle and may be, for example, a crescent or a circle.

The shaft may be reinforced by two coil layers (a first coil layer and a second coil layer) instead of the first braided layer 12 and the second braided layer 14.

In this case, a winding direction of the coil constituting the first coil layer and a winding direction of the coil constituting the second reinforcing layer are inverted to one another, and thus superior torque transmission performance not affected by the rotation direction can be expressed.

Example 1

The guiding catheter 100 that included: the shaft 10 having an effective length of 900 mm formed by layering the inner layer 11 made of PTFE having the inner diameter of 2.24 mm and the thickness of 30 μm, the first braided layer 12 formed of the braided tube produced by weaving a stainless-steel wire (the number of carriers: 16, the number of ends: 1) having a thickness of 40 μm, the intermediate layer 13 made of PEBAX enclosing the sub-lumen 102 having a rectangular cross section (0.30 mm×0.90 mm), the second braided layer 14 formed of the braided tube produced by weaving a stainless-steel wire (the number of carriers: 16, the number of ends: 1) having a thickness of 40 μm, and the outer layer 15 made of PEBAX having the thickness of 53 μm and the outer diameter of 2.97 mm; the balloon 20 made of polyurethane attached to the distal end portion of the shaft 10 having the maximum expansion diameter of 12 mm; the distal end tip 30 made of PEBAX connected to the distal end side of the shaft 10; and the hub 40 connected to the proximal end side of the shaft 10 was manufactured.

Comparative Example 1

A guidewire shaft for comparison was manufactured similarly to Example 1 except that a shaft was formed without disposing the second braided layer 14.
Evaluation for Torque Transmission Performance Each of the guidewire shafts according to Example 1 and Comparative Example 1 was passed through a tube curved in a U shape simulating a blood vessel of a human, and a rotation angle at a distal end side of the shaft when a proximal end side of the shaft was rotated by 0 to 360° around the axis was measured.

Figure 7:
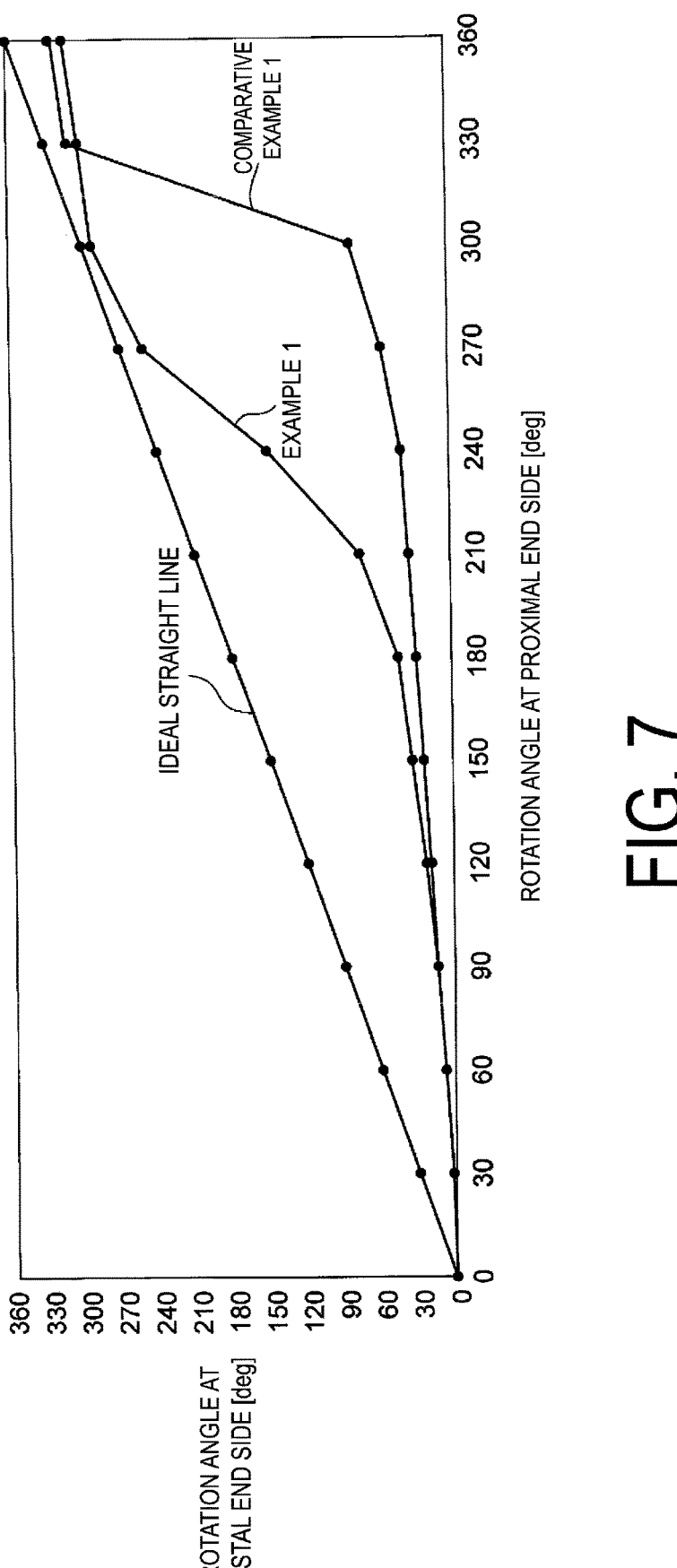
FIG. 7 is a graph showing results of evaluation for torque transmission performance of guidewire shafts according to Example 1 and Comparative Example 1.

FIG. 7 shows the results (the relationship between the rotation angle at the proximal end side of the shaft and the rotation angle at the distal end side of the shaft). The closer to an ideal straight line shown in FIG. 7 the result is, the better the torque transfer performance is.

As illustrated in FIG. 7, it is understood that the guidewire shaft according to Example 1 has dramatically superior torque transmission performance compared to the guidewire shaft according to Comparative Example 1.

Note that, although the same evaluation as described above was performed on a guidewire shaft for comparison manufactured by forming a shaft without disposing the first braided layer 12, the torque transmission performance was inferior to the guidewire shaft according to Example 1.

The invention claimed is:

1. A guiding balloon catheter comprising:
a shaft that includes a main lumen and a sub-lumen;
a balloon that is attached to a distal end portion of the shaft and expands by supplying a fluid flowing through the sub-lumen to an inside of the balloon;
a distal end tip that is connected to a distal end side of the shaft and includes a lumen communicating with the main lumen and opening at a distal end of the distal end tip; and
a hub that is connected to a proximal end side of the shaft and includes ports communicating with the respective main lumen and sub-lumen, wherein
the shaft comprises an inner layer that forms the main lumen, a first reinforcing layer formed on the inner layer, an intermediate layer that is formed on the first reinforcing layer and encloses the sub-lumen, a second reinforcing layer formed on the intermediate layer, and an outer layer formed on the second reinforcing layer from a proximal end of the shaft to a distal end of the shaft;
both of the first reinforcing layer and the second reinforcing layer are braided layers formed of braided tubes that are continuous from the proximal end to the distal end of the shaft,
the shaft has a side hole extending from the sub-lumen in a radial direction of the shaft and communicating with an inside of the balloon, and
the second reinforcing layer extends more toward the distal end of the shaft than the side hole.

2. The guiding catheter according to claim 1, wherein the main lumen is eccentric with respect to a central axis of the shaft, the sub-lumen is formed on a side opposite to a side where the main lumen is eccentric, and a cross-section of the sub-lumen is substantially a rectangle or a crescent.

3. The guiding catheter according to claim 1, wherein the shaft has the distal end portion where shaping is performed in a bent or curved shape.

4. The guiding catheter according to claim 3, wherein the shaping is performed such that the sub-lumen is located outside the bent or curved shape.

5. The guiding catheter according to claim 1, wherein the distal end tip includes a proximal end portion having an outer diameter same as an outer diameter of the shaft and a distal end portion decreasing in diameter in a distal end direction, and a protrusion portion that is inserted into the sub-lumen of the shaft and occludes a distal end opening of the sub-lumen is formed at a proximal end of the distal end tip.

6. The guiding catheter according to claim 5, wherein a ring-shaped contrast marker is inserted into and fitted to the lumen of the distal end tip at the proximal end portion.

* * * * *